United States Patent
Park et al.

(10) Patent No.: US 11,931,566 B1
(45) Date of Patent: Mar. 19, 2024

(54) IMPLANTABLE NERVE STIMULATION DEVICE

(71) Applicant: ENERGY MINING Co., Ltd., Suwon-si (KR)

(72) Inventors: Hyun Moon Park, Gunpo-si (KR); Young Min Cho, Seongnam-si (KR); Jang Mook Jeong, Suwon-si (KR)

(73) Assignee: ENERGY MINING Co., Ltd., Suwon-si (KR)

( * ) Notice: Subject to any disclaimer, the term of this patent is extended or adjusted under 35 U.S.C. 154(b) by 0 days.

(21) Appl. No.: 18/484,999

(22) Filed: Oct. 11, 2023

(30) Foreign Application Priority Data

Dec. 14, 2022 (KR) ........................ 10-2022-0175027

(51) Int. Cl.
*A61N 1/00* (2006.01)
*A61N 1/05* (2006.01)
*A61N 1/375* (2006.01)

(52) U.S. Cl.
CPC ......... *A61N 1/0558* (2013.01); *A61N 1/3754* (2013.01)

(58) Field of Classification Search
None
See application file for complete search history.

(56) References Cited

U.S. PATENT DOCUMENTS

| | | | |
|---|---|---|---|
| 2019/0321644 A1* | 10/2019 | Maharbiz | A61B 5/202 |
| 2021/0268290 A1 | 9/2021 | Sharma et al. | |
| 2023/0135593 A1* | 5/2023 | Kim | A61N 1/3605 |
| | | | 310/300 |

FOREIGN PATENT DOCUMENTS

| | | | |
|---|---|---|---|
| KR | 10-1465001 B1 | 11/2014 | |
| KR | 10-2016-0051016 A | 5/2016 | |
| KR | 102150725 B1 * | 9/2020 | ............... A61N 7/00 |
| KR | 10-2021-0015791 A | 2/2021 | |
| KR | 10-2021-0046358 A | 4/2021 | |
| KR | 10-2348997 B1 | 1/2022 | |
| KR | 10-2022-0082064 A | 6/2022 | |
| WO | WO-2019115217 A1 * | 6/2019 | ........... A61N 1/0556 |

OTHER PUBLICATIONS

"Request for the Submission of an Opinion" Office Action issued in KR 10-2022-0175027; mailed by the Korean Intellectual Property Office dated Feb. 20, 2023.
"Written Decision on Registration" Office Action issued in KR 10-2022-0175027; mailed by the Korean Intellectual Property Office dated May 30, 2023.

* cited by examiner

*Primary Examiner* — John R Downey
*Assistant Examiner* — Anant A Gupta
(74) *Attorney, Agent, or Firm* — Studebaker & Brackett PC

(57) ABSTRACT

The present invention relates to an implantable nerve stimulation device, which includes: a body part which is formed of a metal that ultrasonic waves can be transmitted, and includes a stimulation surface and a charging surface facing each other; a header part which is made of a non-metal and is located at one end of the body part; a cover which includes a stimulation electrode, a hinge part rotatably coupled to one side of the stimulation surface, and a coupling part detachably coupled to the other side of the stimulation surface, is positioned above the stimulation surface to interpose a nerve between the electrode and the stimulation surface; and power generation elements which are located inside the body part and are electrically connected to the electrode.

6 Claims, 10 Drawing Sheets

IMPLANTABLE NERVE STIMULATION DEVICE

CROSS-REFERENCE TO RELATED APPLICATIONS

The present application claims the benefit of priority to Korean Patent Application No. 10-2022-0175027, filed on Dec. 14, 2022, in the Korean Intellectual Property Office, the entire contents of which are hereby incorporated by reference.

BACKGROUND OF THE INVENTION

Field of the Invention

The present disclosure relates to an implantable nerve stimulation device.

Background Art

Neuropathy is a disorder resulting from damage or functional abnormalities in the nervous system, is intractable and has the characteristic of persisting chronically for a long time. As a result, patients suffering from such pain may experience a significant decline in the quality of life, complications such as sleep disorders and depression, and the like.

To treat neuropathy, nerve stimulation therapy which electrically stimulates the nerves is being applied. With the intensification of aging, there is an increasing demand for the nerve stimulation therapy. Accordingly, development of implantable nerve stimulation devices which enable continuous treatment is active.

The implantable nerve stimulation device is transplanted into the body and serves to stimulate the nerves of various organs within the body. For instance, an implantable nerve stimulation device can be transplanted into the neural transmission region within the spine and block stimuli caused by external stimuli or diseases in the body from being transmitted to the cerebrum.

The implantable nerve stimulation device can utilize wireless charging technology based on electromagnetic induction which transmits power signals to a battery built in a housing made of a titanium material. Such wireless charging technology based on the electromagnetic induction may adopt an RFID method, an NFC method, and an MICS-RF method.

However, the wireless charging technology based on the electromagnetic induction has several disadvantages in that it is difficult for the power signals to penetrate the titanium material of the housing, the penetration depth of the power signal into the body is very short, and the charging regions of the body have a restriction in surgical regions or wearing regions, such as the femoral region, the spine region, the sternum, the left clavicle, and so on. Here, the penetration depth of the power signal into the body may be around 1 cm below the skin.

Recently, wireless charging technology using ultrasonic waves as a medium to transmit power signals has been developed. The ultrasound-based wireless charging technology has addressed the problems related to the power signal penetration through the titanium housing and the short penetration depth of the power signals into the body. However, the ultrasound-based wireless charging technology has shortcomings, such as bad transmission efficiency of the power signals, poor battery charging efficiency, heat generation from elements built in the housing, generation of magnetic fields arising from the vibration of the elements, and difficulty in miniaturization due to the need for complex circuitry.

PATENT LITERATURE

Patent Documents

Patent Document 1: Korean Patent No. 10-1465001 (Nov. 19, 2014)

SUMMARY OF THE INVENTION

Accordingly, the present disclosure has been made to solve the above-mentioned problems occurring in the prior arts, and it is an objective of the present disclosure to provide an implantable nerve stimulation device which can enhance implantation depth and allow for miniaturization.

It is another objective of the present disclosure to provide an implantable nerve stimulation device, which supplies power to a stimulation electrode using power generation elements which generate power based on friction from ultrasonic waves, thereby improving the power conversion efficiency of the ultrasonic waves, minimizing heat generation, and reducing the magnetic field generation of the power generation elements.

The objectives of the present disclosure are not limited to those mentioned above, and other objectives not mentioned herein will be clearly understood by those skilled in the art from the following description.

To accomplish the above objectives, according to the present disclosure, there is provided an implantable nerve stimulation device including: a body part which is formed of a metal that ultrasonic waves can be transmitted, and includes a stimulation surface and a charging surface facing each other; a header part which is made of a non-metal and is located at one end of the body part; a cover which includes a stimulation electrode, a hinge part rotatably coupled to one side of the stimulation surface, and a coupling part detachably coupled to the other side of the stimulation surface, is positioned above the stimulation surface to interpose a nerve between the electrode and the stimulation surface; power generation elements which are located inside the body part and are electrically connected to the electrode; a first connection part which extends from the coupling part; a second connection part which is provided at a connection point between the stimulation surface and the charging surface; and a connection member which binds the first connection part and the second connection part, wherein the first connection part includes a plurality of through-holes, a portion of the second connection part is spaced apart from the connection point, and has an insertion space between the portion of the second connection part and the connection point, the connection member includes a medical wire which continuously passes through at least one of the plurality of through-holes and the insertion space to bind and tighten the first connection part and the second connection part, and the power generation elements generate power based on friction caused by ultrasonic waves penetrating the charging surface, and includes an inducer vibrating by the ultrasonic waves, an electrified body generating frictional electricity by friction with the inducer, and a spacer interposed between the inducer and the electrified body to mutually separate the inducer and the electrified body.

Moreover, the stimulation surface is covered with a non-metallic coating layer.

Furthermore, the non-metallic coating layer includes silicon.

Additionally, the stimulation surface has a shape curved toward the inside of the body part, and the charging surface has a flat shape.

In addition, the cover has a shape curved in a direction of moving away from the stimulation surface.

Additionally, the cover can include: a hinge part which is located on one side of the cover and rotatably coupled to one side of the stimulation surface; and a coupling part which is located on the other side of the cover and detachably coupled to the other side of the stimulation surface.

Furthermore, the cover can further include: a first connection part extending from the coupling part; a second connection part provided at the connection point between the stimulation surface and the charging surface; and a connection member binding the first connection part and the second connection part.

Additionally, the first connection part includes a plurality of through-holes, and an insertion space formed between a portion of the second connection part, which is spaced apart from the connection point, and the connection point. The connection member can bind the first connection part and the second connection part by continuously passing through one of the multiple through-holes and the insertion space.

In addition, the power generation elements can generate power based on the friction caused by the ultrasonic waves penetrating the charging surface.

Moreover, the stimulation electrode has a pattern shape with two or more curved portions.

Other specific details of the present disclosure are included in the detailed description and drawings.

The implantable nerve stimulation device according to an embodiment of the present disclosure can enhance implantation depth and allow for miniaturization.

Moreover, the implantable nerve stimulation device according to an embodiment of the present disclosure supplies power to a stimulation electrode using power generation elements which generate power based on friction from ultrasonic waves, thereby improving the power conversion efficiency of the ultrasonic waves, minimizing heat generation, and reducing the magnetic field generation of the power generation elements.

Furthermore, the implantable nerve stimulation device according to an embodiment of the present disclosure does not need for a separate device for electromagnetic radiation by reducing electromagnetic radiation due to the friction and vibration of the power generation elements.

The advantages of the present disclosure are not limited to the above-mentioned advantages, and other advantages, which are not specifically mentioned herein, will be clearly understood by those skilled in the art from the following description.

DETAILED DESCRIPTION OF THE PREFERRED EMBODIMENT

Advantages and features of the present disclosure and methods accomplishing the advantages and features will become apparent from the following detailed description of exemplary embodiments with reference to the accompanying drawings. However, the present disclosure is not limited to exemplary embodiment disclosed herein but will be implemented in various forms. The exemplary embodiments are provided so that the present disclosure is completely disclosed, and a person of ordinary skilled in the art can fully understand the scope of the present disclosure. Therefore, the present disclosure will be defined only by the scope of the appended claims.

Terms used in the specification are used to describe specific embodiments of the present disclosure and are not intended to limit the scope of the present disclosure. In the specification, the terms of a singular form may include plural forms unless otherwise specified. It should be also understood that the terms of 'include' or 'have' in the specification are used to mean that there is no intent to exclude existence or addition of other components besides components described in the specification. In the detailed description, the same reference numbers of the drawings refer to the same or equivalent parts of the present disclosure, and the term "and/or" is understood to include a combination of one or more of components described above. It will be understood that terms, such as "first" or "second" may be used in the specification to describe various components but are not restricted to the above terms. The terms may be used to discriminate one component from another component. Therefore, of course, the first component may be named as the second component within the scope of the present disclosure.

Unless otherwise defined, all terms (including technical and scientific terms) used herein have the same meaning as commonly understood by those skilled in the technical field to which the present disclosure pertains. It will be further understood that terms, such as those defined in commonly used dictionaries, should not be interpreted in an idealized or overly formal sense unless expressly so defined herein.

Hereinafter, preferred embodiments of the present disclosure will be described in detail with reference to the accompanying drawings.

Figure 1:
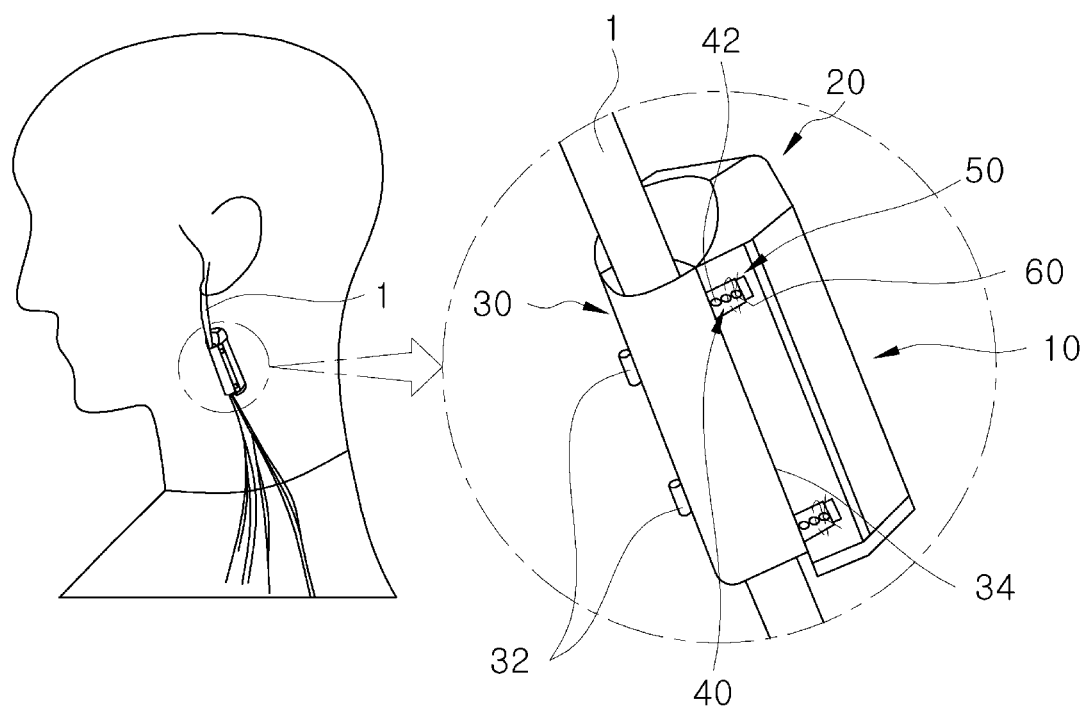
FIG. 1 is a schematic diagram illustrating a state in which an implantable nerve stimulation device according to an embodiment of the present disclosure is installed within the body.
Figure 2:
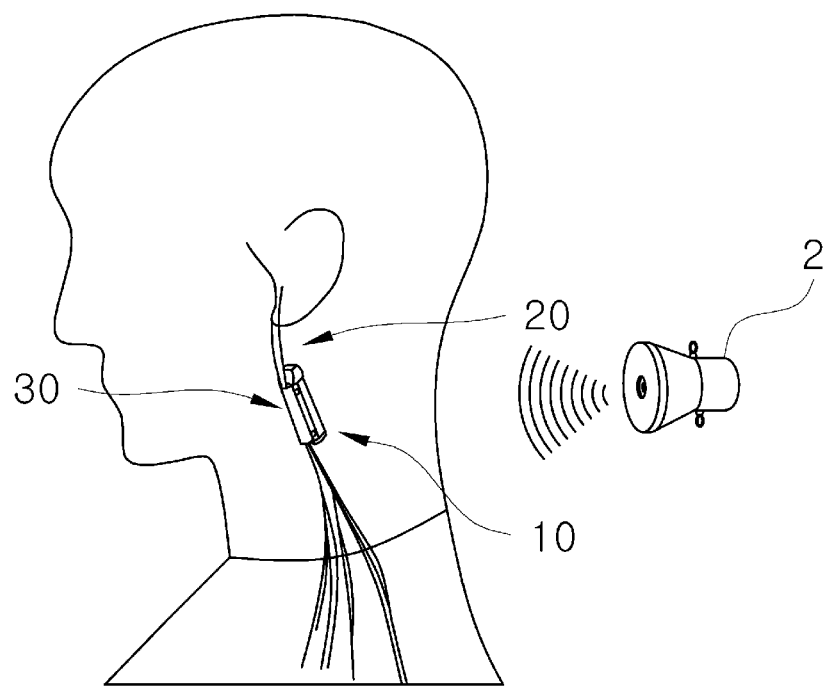
FIG. 2 is a schematic diagram illustrating a state in which ultrasonic waves are transmitted to the implantable nerve stimulation device according to an embodiment of the present disclosure.
Figure 3:
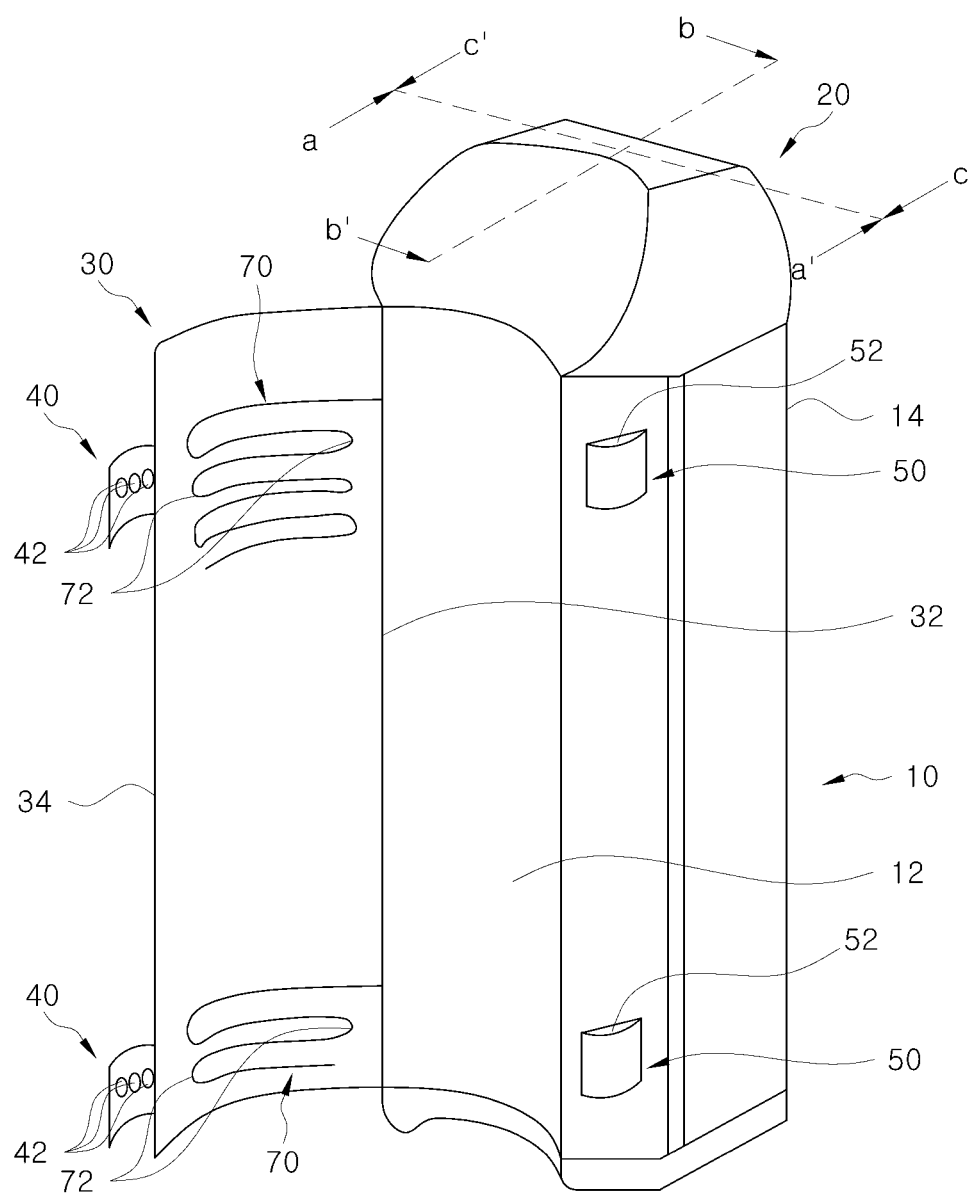
FIG. 3 is a schematic diagram illustrating a state in which a cover of the implantable nerve stimulation device according to an embodiment of the present disclosure is opened.
Figure 4:
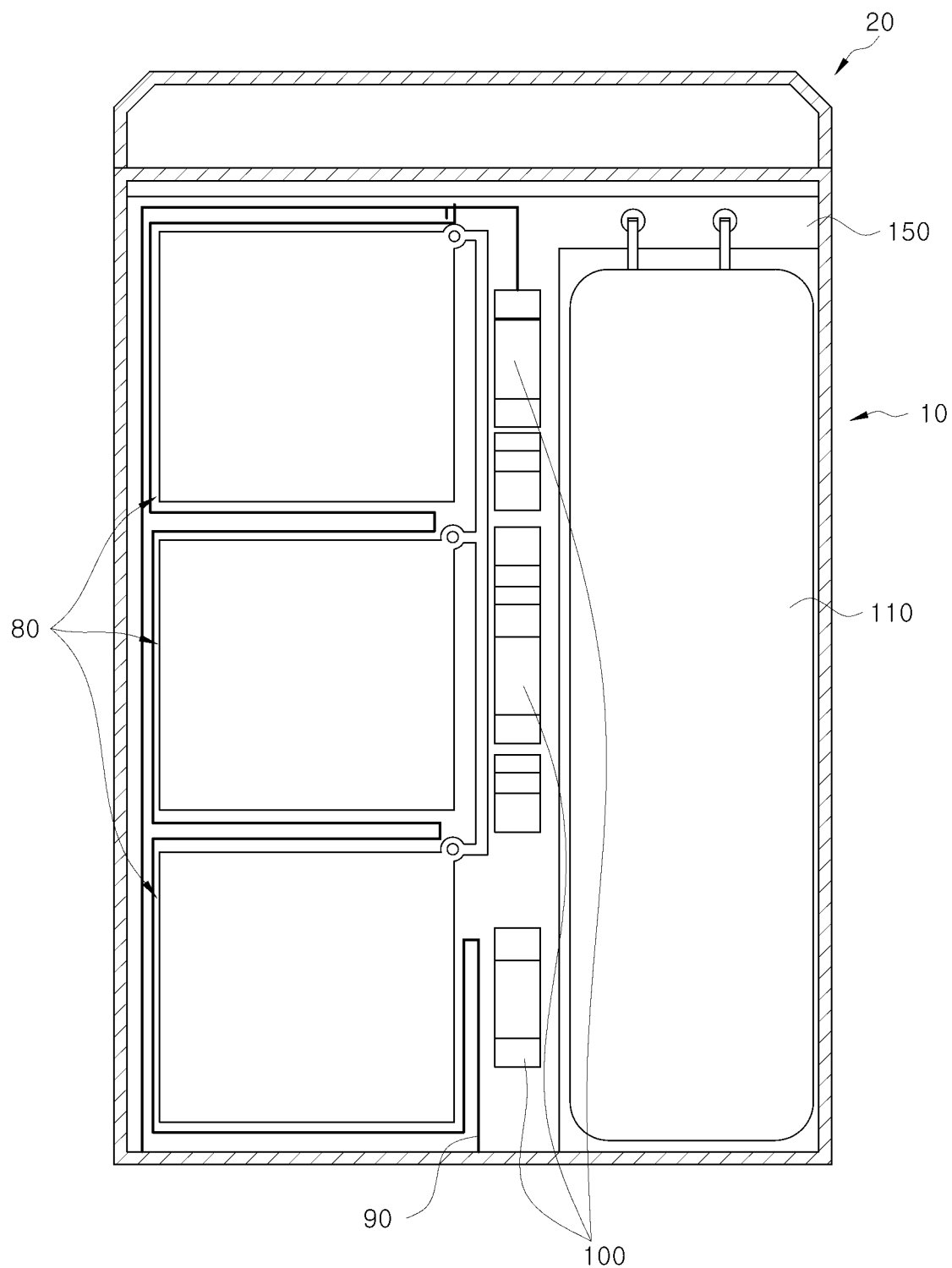
FIG. 4 is a cross-sectional view taken along the line a-a' of FIG. 3.
Figure 5:
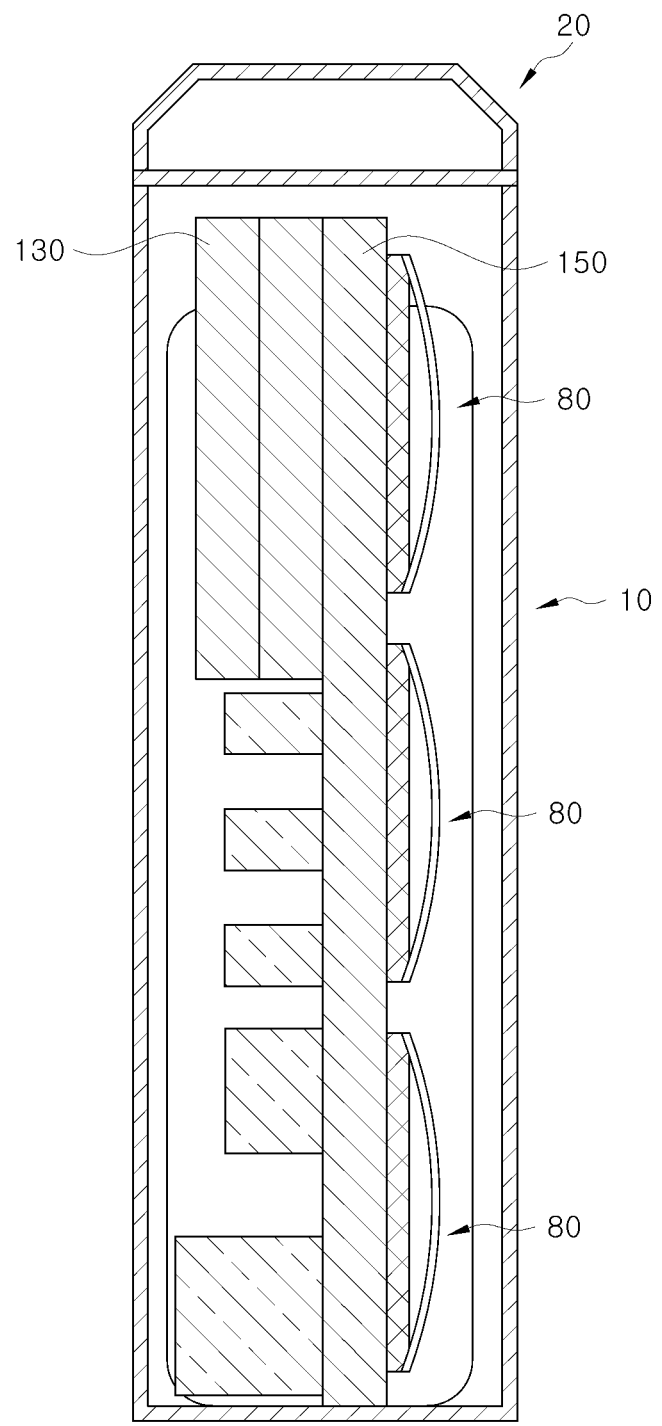
FIG. 5 is a cross-sectional view taken along the line b-b' of FIG. 3.
Figure 6:
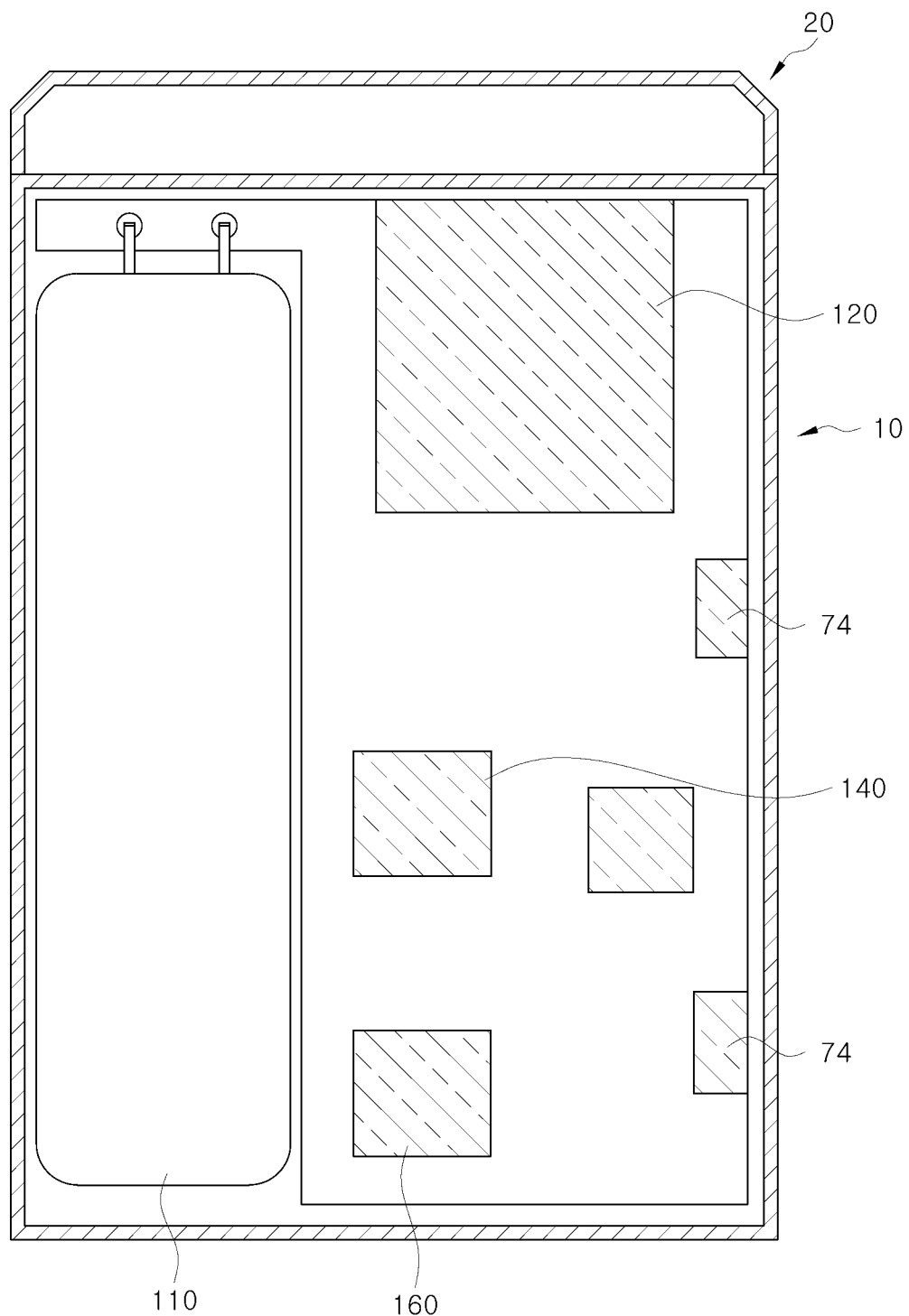
FIG. 6 is a cross-sectional view taken along the line c-c' of FIG. 3.

FIG. 1 is a schematic diagram illustrating a state in which an implantable nerve stimulation device according to an embodiment of the present disclosure is installed within the body, FIG. 2 is a schematic diagram illustrating a state in which ultrasonic waves are transmitted to the implantable nerve stimulation device according to an embodiment of the present disclosure, FIG. 3 is a schematic diagram illustrating a state in which a cover of the implantable nerve stimulation device according to an embodiment of the present disclosure is opened, FIG. 4 is a cross-sectional view taken along the line a-a' of FIG. 3, FIG. 5 is a cross-sectional view taken along the line b-b' of FIG. 3, and FIG. 6 is a cross-sectional view taken along the line c-c' of FIG. 3.

As shown in FIGS. 1 through 6, the implanted nerve stimulation device according to an embodiment of the present disclosure includes a body part 10, a header part 20, a cover 30, and power generation elements 80.

The body part 10 serves as a main body of the present disclosure, and can function as a housing for accommodating the power generation elements 80. The body part 10 is formed of a metal that ultrasonic waves can be transmitted, and can include a stimulation surface 12 and a charging surface 14 which face each other. Here, the metal that ultrasonic waves can be transmitted can be a biocompatible material such as titanium. However, other than titanium, the metal that ultrasonic waves can be transmitted can be other materials that are ultrasonically transmissive and biocompatible, and the present disclosure is not limited thereto.

The stimulation surface 12 of the body part 10, in conjunction with the cover 30 which will be described later, can allow the internal nerve 1 to be interposed (Refer to FIGS. 1 through 3). In other words, the internal nerve 1 can be interposed between the stimulation surface 12 and the cover 30.

For instance, the stimulation surface 12 can be provided on one side of the body part 10, and the one side of the body part 10 may be the front side of the body part 10.

In another example, the stimulation surface 12 can be covered with a non-metallic coating layer. As described above, since the stimulation surface 12 can be covered with a non-metallic coating layer, discomfort applied to the internal nerve 1 interposed between the stimulation surface 12 and the cover 30 can be reduced. Here, the non-metallic coating layer covering the stimulation surface 12 may include silicon. However, besides silicon, the non-metallic coating materials may be other biocompatible materials, and the present disclosure is not limited thereto.

In yet another example, the stimulation surface 12 can have a shape curved toward the inside of the body part 10. Therefore, the internal nerve 1 can be easily interposed between the stimulation surface 12 and the cover 30.

Meanwhile, the stimulation surface 12 and the cover 30 are coupled by a first connector 40, a second connector 50, and a connection member 60, which will be described later, and can fix the internal nerve 1 interposed between the stimulation surface 12 and the cover 30. Further details on the above will be described later.

The charging surface 14 can receive ultrasonic waves emitted from a transducer 2. The ultrasonic waves transmitted to the charging surface 14 are utilized as an energy source for generating power in the power generation elements 80 located inside the body part 10. Further details on the above will be described later (Refer to FIG. 2).

For example, the charging surface 14 can be provided on the other side of the body part 10 facing the one side, and the other side of the body part 10 may be the rear side of the body part 10.

In another example, the charging surface 14 may have a flat shape.

The header part 20 is formed of a non-metallic material, and can be located on one end of the body part 10. As described above, since the header part 20 is formed of non-metallic material, various signals transmitted to and received from the power management unit 140, which will be described later, can easily pass through. Additionally, after being positioned on one end of the body part 10, the header part 20 can be detachably coupled to the end of the body part 10.

For example, the one end of the body part 10 where the header part 20 is located can be the top of the body part 10.

In another example, the one side of the header part 20 facing the internal nerve 1 may have a shape curved toward the inside of the body part 10. Therefore, when the header part 20 is placed adjacent to the internal nerve 1, it can prevent the header part 20 from giving damage to the internal nerve 1.

The cover 30, in conjunction with the stimulation surface 12 of the body part 10, can allow the internal nerve 1 to be interposed.

The cover 30 includes a stimulation electrode 70 and can be placed on top of the stimulation surface 12 of the body part 10 so that the nerve 1 is interposed between the stimulation electrode 70 and the stimulation surface 12.

For instance, the cover 30 may have a shape curved in a direction of moving away from the stimulation surface 12 when placed on top of the stimulation surface 12. Therefore, when the internal nerve 1 is interposed between the stimulation surface 12 of the body part 10 and the cover 30, the cover 30 can reduce damage or discomfort to the internal nerve 1.

The cover 30 may include a hinge part 32 and a coupling part 34.

The hinge part 32 is provided on one side of the cover 30, and can be rotatably connected to one side of the stimulation surface 12. Here, the one side of the cover 30 where the hinge part 32 is provided can be the left side of the cover 30, and the one side of the stimulation surface 12 to which the hinge part 32 is rotatably connected can be the left side of the stimulation surface 12.

For example, the hinge part 32 may include a hinge shaft which is rotatably connected to the one side of the stimulation surface 12.

The coupling part 34 is provided on the other side of the cover 30, and can be detachably connected to the other side of the stimulation surface 12. Here, the other side of the cover 30 where the coupling part 34 is provided can be the right side of the cover 30, and the other side of the stimulation surface 12 to which the coupling part 34 is detachably connected can be the right side of the stimulation surface 12.

The coupling part 34 can be detachably connected to the other side of the stimulation surface 12 by the first connection part 40, the second connection part 50, and the connection member 60.

The first connection part 40 can extend from the coupling part 34. The first connection part 40 can extend in a direction of moving away from the cover 30. For instance, the first connection part 40 can have a strap-like shape.

The second connection part 50 can be provided at a connection point between the stimulation surface 12 and the charging surface 14 of the body part 10. For example, the second connection part 50 can have a strap-like shape.

The connection member 60 can serve to bind the first connection part 40 and the second connection part 50. For instance, the connection member 60 may be a medical wire.

For example, the first connection part 40 may include a plurality of through-holes 42. Additionally, a portion of the second connection part 50 can be spaced apart from the connection point between the stimulation surface 12 and the charging surface 14 of the body part 10, and create an insertion space 52 between the portion of the second connection part 50 and the connection point. In addition, the connection member 60 can continuously pass through one of the plurality of through-holes 42 and the insertion space 52 and bind and tighten the first connection part 40 and the second connection part 50. Therefore, when the connection member 60 bind and tighten the first connection part 40 provided on the cover 30 to the second connection part 50 provided on the body part 10, the internal nerve 1 can be fixed between the stimulation surface 12 of the body part 10 and the cover 30.

Furthermore, the plurality of through-holes 42 can be formed at intervals in the length direction of the first connector 40. Moreover, as both ends of the second connector 50 are coupled to the connected portion between the stimulation surface 12 and the charging surface 14 of the body part 10, the insertion space 52 can be formed between a portion of the second connector 50 and the connected portion.

The stimulation electrode 70 can serve to apply electrical stimulation to the internal nerve 1. Here, the width or the phase of the electrical stimulation applied by the stimulation electrode 70 can be controlled by the power management unit 140, which will be described later.

For instance, the stimulation electrode 70 can have a pattern shape with two or more curved portions. The stimulation electrode 70 can have a zigzag shape.

In another example, the stimulation electrode 70 can apply electrical stimulation to the internal nerve 1 based on power supplied from the power generation elements 80, which will be described later.

In yet another example, the stimulation electrode 70 can apply electrical stimulation to the internal nerve 1 based on power supplied from the power management unit 140, which will be described later.

The power generation elements 80 are located inside the body part 10, and can be electrically connected to the stimulation electrode 70. The power generation elements 80 can generate power based on the friction caused by ultrasonic waves passing through the charging surface 14. In this instance, the friction electricity generated by the power generation elements 80 can be transmitted to the power management unit 140 and the stimulation electrode 70.

Therefore, the implantable nerve stimulation device according to an embodiment of the present disclosure can improve the insertion depth into the body and achieve miniaturization since the power generation elements 80 perform power generation based on friction by the ultrasonic waves passing through the charging surface 14.

Additionally, the implantable nerve stimulation device according to an embodiment of the present disclosure supplies power to the stimulation electrode 70 using a power generation elements 80 based on friction from ultrasonic waves, thereby enhancing the power conversion efficiency of ultrasonic waves and preventing heat generation. In addition, the implantable nerve stimulation device according to an embodiment of the present disclosure can reduce errors due to electromagnetic radiation generated from the friction and vibration of the power generation elements 80.

For instance, the plurality of power generation elements 80 can be spaced apart within the body part 10 at intervals.

In another example, the power generation elements 80 can have a rectangular shape.

In yet another example, the power generation elements 80 can have a disc shape.

Figure 7:
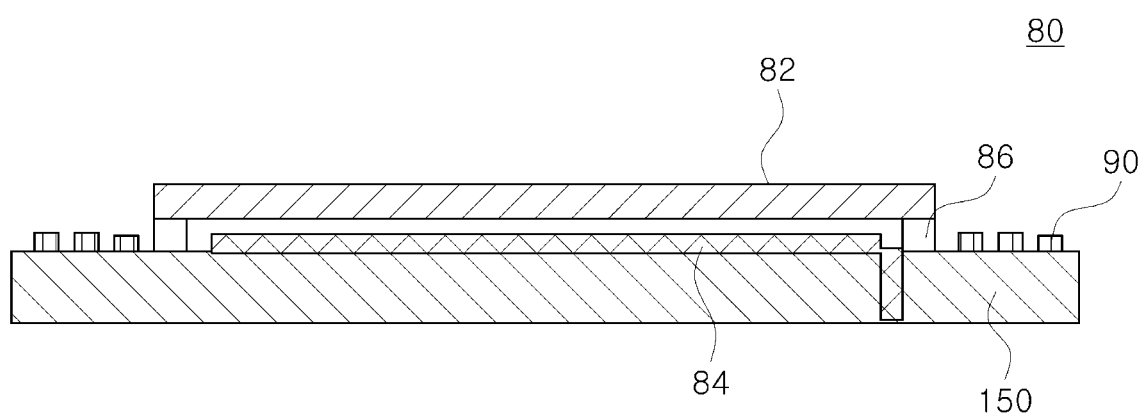
FIG. 7 is a cross-sectional view illustrating power generation elements of the implantable nerve stimulation device according to an embodiment of the present disclosure.

FIG. 7 is a cross-sectional view showing power generation elements 80 of the implantable nerve stimulation device according to an embodiment of the present disclosure.

As illustrated in FIG. 7, each of the power generation elements 80 may include an inducer 82, an electrified body 84, and a spacer 100. The power generation element 80 can generate friction electricity due to the friction between the inducer 82 and the electrified body 84.

The inducer 82 can vibrate by ultrasonic waves, and generate friction electricity by friction with the electrified body 84 while repeating contact with and separation from the electrified body 84.

For example, the inductor 82 may include a material which can easily vibrate by ultrasonic waves. Here, the material which can easily vibrate by ultrasonic waves may include fluoroplastic-based materials. For instance, the fluoroplastic-based materials may include poly tetra fluoro ethylene (PTFE), perfluoroalkoxy (PFA), Fluorinated ethylene propylene (FEP), polychlorotrifluoroethylene (PCTF), ethylene tetra fluoro ethylene (ETFE), ethylene-chloro trifluoro ethylene (ECTFE), polyvinylidene fluoride (PVDF), polyvinylfluoride (PVF), poly vinyl chloride (PVC), and polyethylene (PE). However, the material which can easily vibrate by ultrasonic waves may also be applied from materials other than the fluoroplastic-based materials.

The electrified body 84 can generate friction electricity by friction with the inductor 82. The electrified body 84 may act as a conductor to transmit the friction electricity generated by friction with the inductor 82 to the power management unit 140 which will be described later. The power management unit 140 can charge the battery 110 by transmitting the friction electricity sent from the electrified body 84, or can operate the stimulation electrode 70 by transferring the friction electricity from the electrified body 84.

For example, the electrified body 84 may include a material which can easily generate friction electricity due to the friction with the inductor 82. Here, the material which can easily generate friction electricity can be nickel, gold, silver, etc.

The spacer 100 is interposed between the inductor 82 and the electrified body 84 to separate the inductor 82 and the electrified body 84. The reason that the spacer 100 separates the inductor 82 and the electrified body 84 is to prevent that the inductor 82 and the electrified body 84 are not separated from each other after they are adhered to each other due to the friction between the inductor 82 and the electrified body 84.

Hereinafter, a process by which the nerve stimulation device according to an embodiment of the present disclosure stimulates the internal nerves will be described. The following process can be carried out by a robotic arm or an operator.

First, an incision is made on the skin adjacent to the nerves of a patient to form an incision window, the implantable nerve stimulation device is inserted through the incision window, and the internal nerves 10 are placed between the stimulation surface 12 of the body 10 and the cover 30. In this instance, the connection member 60 can continuously pass through one of the plurality of through-holes 42 of the first connecting part 40 provided on the cover 30 and the insertion space 52 of the second connection part 50 provided at the connection point between the stimulation surface 120 and the charging surface 140 of the body 10, and can bind and tighten the first connection part 40 and the second connection part 50. Subsequently, the incision window made on the patient is sutured.

Next, the transducer 2 emits ultrasonic waves towards the charging surface 14 of the body 10.

Thereafter, the power generation elements 80 generate power based on the friction from the ultrasonic waves penetrating the charging surface. In this instance, the power generated by the power generation units 80 is transmitted to the stimulation electrode 70.

Finally, based on the power transferred from the power generation elements 80, the stimulation electrode 70 applies an electrical stimulation to the internal nerve 1. The stimulation electrode 70 can be controlled by the power management unit 140, which will be detailed later.

On the other hand, not only the friction electricity but also the magnetic field can be generated from the power generation elements 80 due to the friction between the inductor 82 and the electrified body 84. In this instance, as the vibration frequency of the ultrasonic waves sent to the power generation elements 80 increases, the magnitude of the magnetic field generated by the power generation elements 80 increases. The magnetic field can interfere with the communication of the communication module which will be described later.

Therefore, the implantable nerve stimulation device according to an embodiment of the present disclosure may further include a magnetic field absorption part 90 which absorbs the magnetic field generated by the power generation elements 80.

The magnetic field absorption part 90 is arranged around the perimeter of the power generation element 80 and can absorb the magnetic field generated by the power generation element 80. The magnetic field absorption part 90 may include a material capable of absorbing a magnetic field. For example, the material capable of absorbing a magnetic field can include aluminum, copper, nickel, silver, zinc oxide, tin oxide, aluminum, or the like. However, the material capable of absorbing the magnetic field is not limited to aluminum, copper, nickel, silver, zinc oxide, tin oxide, and aluminum, but can also be applied to other materials which the magnetic field can pass through, and the present disclosure is not limited thereto.

For example, the magnetic field absorption part 90 may have a pattern shape that wraps around the perimeter of the power generation elements 80. Here, the pattern shape may have a zigzag form. The magnetic field absorption part 90 can also block electromagnetic waves emitted around the perimeter of the power generation elements 80.

When the magnetic field absorption part 90 is placed in an area where a magnetic field occurs, for example, around a magnetic resonance imaging (MRI) device or an electric vehicle, the magnetic field absorption part 90 can absorb the magnetic field of the area where the magnetic field occurs, thereby minimizing the impact of the magnetic field in the area, in which the magnetic field occurs, on a user and preventing malfunction.

On the other hand, when the magnetic field generated by the power generation elements 80 is absorbed by the magnetic field absorption part 90, the energy securing efficiency of energy generated from the power generation elements 80 may decrease. Therefore, the implantable nerve stimulation device according to an embodiment of the present disclosure can maximize energy securing efficiency by converting the magnetic field generated from the power generation elements 80 and absorbed by the magnetic field absorption part 90 into electricity. To this end, the implantable nerve stimulation device according to an embodiment of the present disclosure may further include a power management unit 140, which will be described in detail later.

Figure 8:
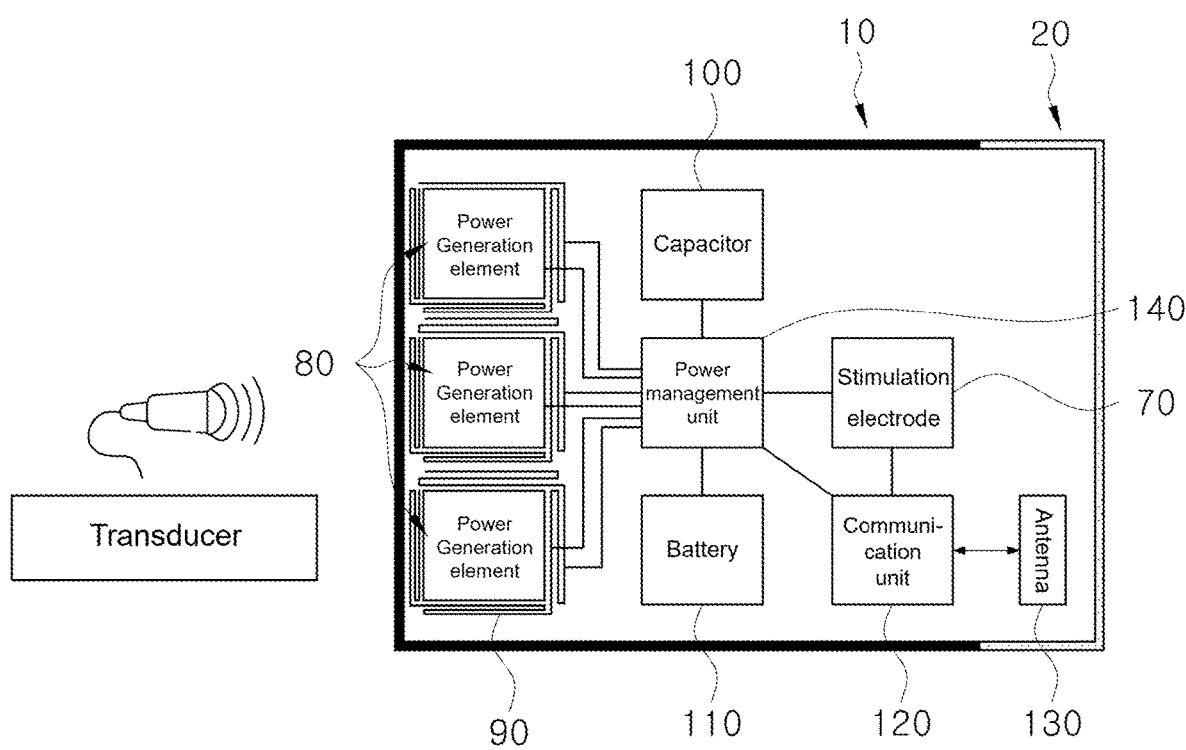
FIG. 8 is a block diagram illustrating the implantable nerve stimulation device according to an embodiment of the present disclosure.

FIG. 8 is a block diagram illustrating the implantable nerve stimulation device according to an embodiment of the present disclosure.

As illustrated in FIG. 8, the implantable nerve stimulation device according to an embodiment of the present disclosure may include a capacitor 100, a battery 110, a communication part 120, an antenna 130, and a power management unit 140. The power generation element 80, the capacitor 100, the battery 110, the communication part 120, the antenna 130, and the power management unit 140 can be arranged to be spaced apart on a circuit board 150 embedded in the body part 10 and can be electrically connected to each other.

The capacitor 100 can store electricity from the friction electricity transferred from the power generation element 80 and the magnetic field transferred from the magnetic field absorption part 90. In this instance, the magnetic field transferred from the magnetic field absorption part 90 to the capacitor 100 can be transferred to the capacitor 100 after being converted into electricity by the power management unit 140 arranged between the magnetic field absorption part 90 and the capacitor 100. Meanwhile, the type of electricity stored in the capacitor 100 may be direct current (DC).

For example, the capacitor 100 can reduce the voltage of the power converted by friction electricity and a magnetic field to boost the current. The reason the capacitor 100 boosts the current is that the current of the power converted by the friction electricity and the magnetic field is very low, from tens of nA to hundreds of uA, and the voltage of tens of V is generated. Accordingly, to effectively charge the battery 110, voltage can be reduced to match the battery characteristics, between 2.8V to 4.2V, and the current can be boosted to a possible mA or tens of mA for efficient charging of the battery 110.

In another example, the capacitor 100 can be configured in plurality, and the plurality of capacitors 100 can be arranged in series. Additionally, the plurality of capacitors 100 can be arranged in a multi-stage manner.

The battery 110 can be charged by the power transferred from the capacitor 100. The power charged in the battery 110 can be transferred to at least one of the communication unit 120 and the stimulation electrode 70 under the control of the power management unit 140. Meanwhile, the battery 110 can be replaced with a super capacitor 100.

The power management unit 140 can transfer the frictional electricity transmitted from the power generation device 80 to the capacitor 100 as power and convert the magnetic field transferred from the magnetic field absorption unit 90 into power and transfer the power to the capacitor 100. Here, the power management unit 140 can have a magnetic field conversion device (not illustrated) which converts the magnetic field transferred from the magnetic field absorption unit 90 into power. For example, the magnetic field conversion device can include a magnetic wave device, a piezoelectric device, etc.

The power management unit 140 can control whether the power stored in the capacitor 100 is transferred to the battery 110, the stimulation electrode 70, and the communication unit 120 based on the amount of power stored in the capacitor 100. For instance, when the amount of power stored in the capacitor 100 exceeds a pre-set power threshold, the power management unit 140 can control the capacitor 100 so that the power stored therein is transferred to the battery 110, the stimulation electrode 70, and the communication unit 120. In addition, when the amount of power stored in the capacitor 100 is less than or equal to the pre-set power threshold, the power management unit 140 can control the capacitor 100 so that the stored power is not transferred to the battery 110, the stimulation electrode 70, and the communication unit 120.

When the amount of power stored in the capacitor 100 is less than or equal to a pre-set power threshold, the power management unit 140 can also control whether the power stored in the battery 110 is transferred to the stimulation electrode 70 and the communication unit 120 based on the amount of power stored in the battery 110. For instance, when the amount of power stored in the battery 110 exceeds a pre-set power threshold, the power management unit 140 can control the battery 110 so that the power stored therein is transferred to the stimulation electrode 70 and communication unit 120. Moreover, when the amount of power stored in the battery 110 is less than or equal to the pre-set power threshold, the power management unit 140 can control the capacitor 100 so that the stored power in the battery 110 is not transferred to the stimulation electrode 70 and communication unit 120.

The power management unit 140 can also transmit power data, which includes the amount of power applied to the stimulation electrode 70, the amount of power stored in the capacitor 100, and the amount of power stored in the battery 110, to the communication unit 120.

The communication unit 120 acts as a wireless communication network connecting the power management unit 140 and a monitoring unit wirelessly. Therefore, the power data transmitted from the power management unit 140 to the communication unit 120 can be transferred to the monitoring unit through the communication unit 120. Here, the monitoring unit can display the amount of power applied to the stimulation electrode 70, the amount of power stored in the capacitor 100, and the amount of power stored in the battery 110 on a screen. Additionally, the monitoring unit can remotely control the power management unit 140, the stimulation electrode 70, the capacitor 100, the battery 110, and pulse-based nerve stimulation. For example, the monitoring unit can include a microcomputer, a user terminal, etc.

As an example, the communication unit 120 can include not only a wifi module and a wireless broadband module but also wireless communication modules which support various wireless communication methods, such as wireless body area network (WBAN), medical device radiocommunications service (MedRadio), global system for mobile communication (GSM), code division multiple access (CDMA), wideband code division multiple access (WCDMA), universal mobile telecommunications system (UMTS), time division multiple access (TDMA), long term evolution (LTE), 4G, 5G, 6G, etc.

The antenna 130 converts various signals transmitted and received between the communication unit 120 and an external server into radiowaves for transmission and reception.

Meanwhile, a converter 160 may be provided on the circuit board 150 and be electrically connected between the power management unit 140 and the capacitor 100 to convert alternating current received from the power management unit 140 into direct current.

Furthermore, an electrode terminal 74 may be provided on the circuit board 150 and be electrically connected to the stimulation electrode 70 to apply power transmitted from the capacitor 100 or the battery 110 to the stimulation electrode 70.

The electrical circuit of the power management unit 140 will be described in detail below.

Figure 9:
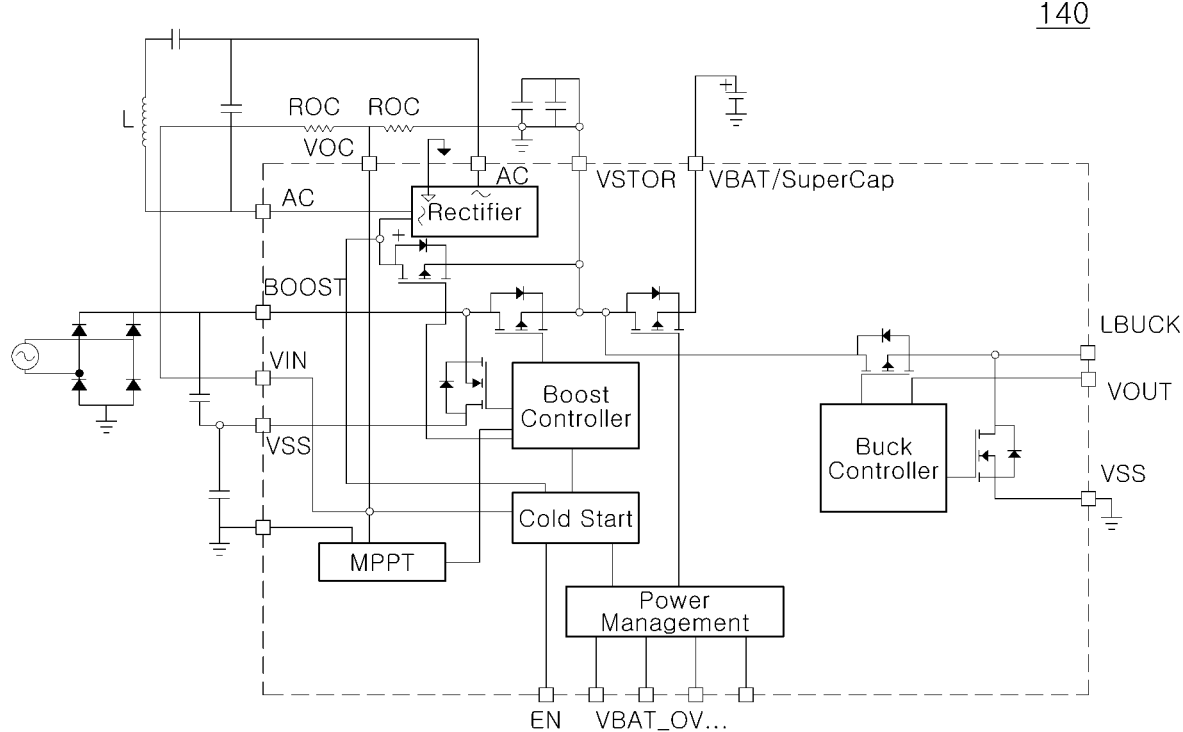
FIG. 9 is an electrical circuit diagram of a power management unit of the implantable nerve stimulation device according to an embodiment of the present disclosure.

FIG. 9 is an electrical circuit diagram of the power management unit 140 of the implantable nerve stimulation device according to an embodiment of the present disclosure.

Referring to FIG. 9, a rectifier of the power management unit 140 can convert the alternating current (AC) from the power converted from the magnetic field into direct current (DC). The rectifier can be built into the body part 10 or can be provided on the outside of the body part 10. In a case in which the rectifier is provided on the outside of the body part 10, only a positive terminal of the rectifier can be connected to a boost controller. Here, power information of the positive terminal of the rectifier is transmitted to a cold start unit and the boost controller, and the cold start unit can compare two input data (the frictional electric value transferred from the power generation elements 80 to the power management unit 140 and the magnetic field value transferred from the magnetic field absorption part 90 to the power management units 140).

Furthermore, an EN of the power management unit 140 can be connected to the stimulation electrode 70 and an MCU, can define the function of a connected load device through high or low operation messages.

Additionally, the AC of the power management unit 140 is a port connected to the magnetic field absorption part 90, and can be connected to an internal rectifier of the power management unit 140.

The cold start unit of the power management unit can control the charging status of the battery 110. The cold start unit of the power management unit 140 has the following features.

First, the cold start unit of the power management unit 140 monitors and compares two input data (the frictional electric value from the power generation element 80 to the power management unit 140 and the magnetic field value from the magnetic field absorption part 90 to the power management unit 140). Second, the cold start unit of the power management unit influences the boost controller by comparing the two input data. Third, the cold start unit of the power management unit transfers information to an nerve stimulation IC or the MCU through the EN (Enable) PIN. Fourth, the cold start unit of the power management unit includes a process of comparing the two input data, and depending on the compared value of the two input data, can be linked to switch control of the boost controller.

Figure 10:
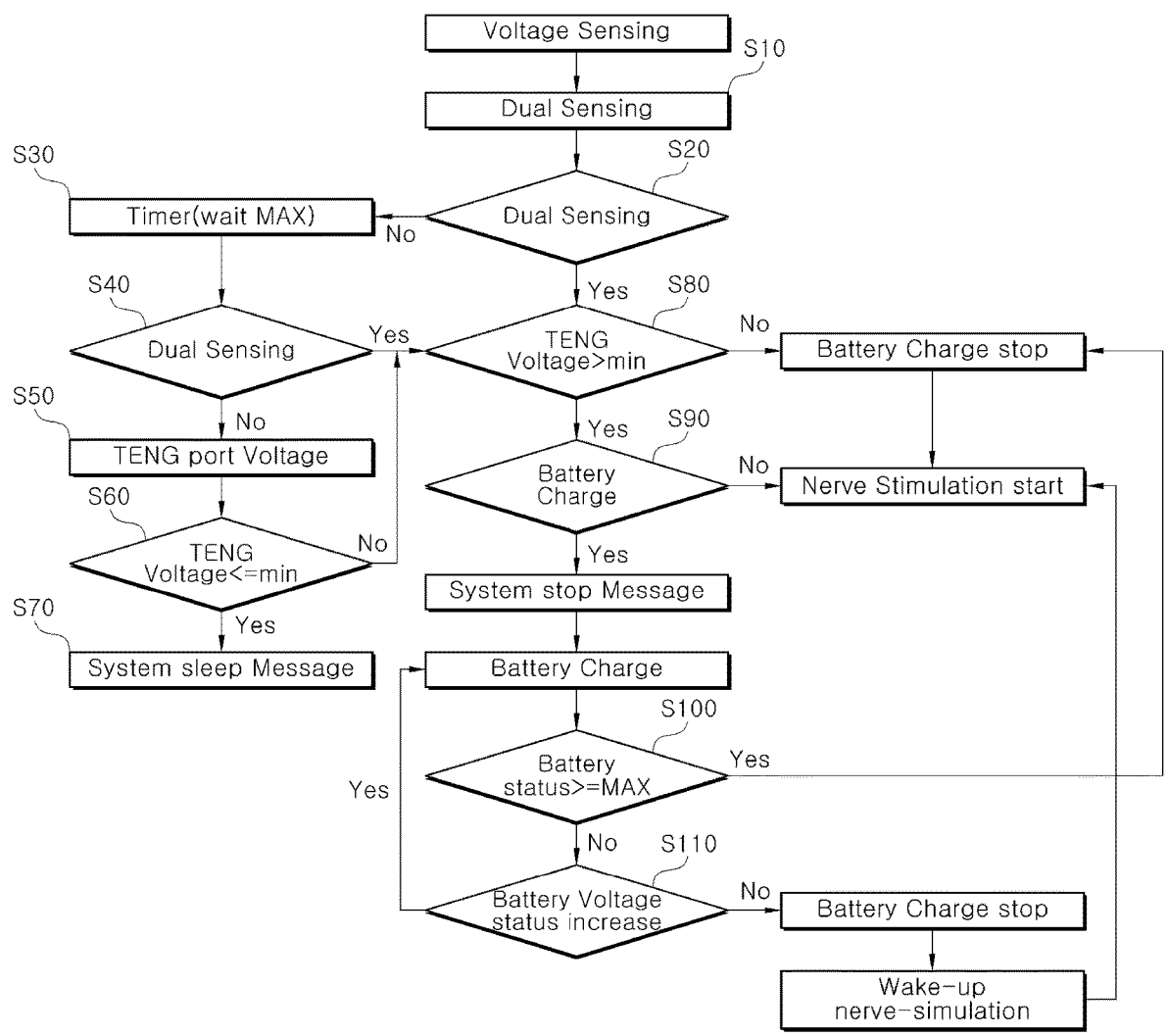
FIG. 10 is a flowchart illustrating a control process of a cold start of the power management unit of the implantable nerve stimulation device according to an embodiment of the present disclosure.

FIG. 10 is a flowchart illustrating a control process of the cold start of the power management unit 140 of the implantable nerve stimulation device according to an embodiment of the present disclosure.

As illustrated in FIG. 10, the cold start unit of the power management unit 140 can have the following control process.

First, voltage is measured from each of the two input data (the frictional electric value transferred from the power generation element 80 to the power management unit 140 and the magnetic field value transferred from the magnetic field absorption part 90 to the power management unit 140) (S10).

Next, when the voltage is not measured from each of the two input data (the frictional electric value from the power generation element 80 to the power management unit 140 and the magnetic field value from the magnetic field absorption part 90 to the power management unit 140) (S20), additional monitoring is performed for a few seconds through a timer (wait MAX) (S30). The reason for additional monitoring through the timer is that, when the ultrasonic energy transferred from the transducer 2 to the power generation elements 80 is too low for the power generation element 80 to generate power, it takes several seconds for the power management unit 140 to measure the two generated input data.

Next, measurement (dual sensing) of the two input data is performed (S40).

When both input data are measured, the power stored in the capacitor 100 is transferred to the battery 110 for battery charging (S90).

Additionally, if both input data are not measured (dual sensing, No), the voltage of the power generated by the power generation elements 80 is measured (S50).

If the voltage measurement value of the power generated from the power generation elements 80 is below the set minimum value (min) (S60), the power management unit 140 sends a system sleep message to the stimulation electrode 70 (S70). In this instance, the stimulation electrode 70 transmits the message to the communication unit 120.

In addition, when the voltage measurement value of the power generated from the power generation element 80 exceeds the set minimum value (S80), since the battery 110 can be charged or the device can be operated, the power stored in the capacitor 100 is transferred to the battery 110 for battery charging (S90). In this instance, the operation of the stimulation electrode 70 is stopped.

On the other hand, when the voltage of the battery 110 measured by the power management of the power management unit 140 during battery charging exceeds the set maximum value, the battery 110 is not charged through the boost controller and the power management of the power management unit 140 (S100).

Next, a battery voltage status increase management unit of the power management unit 140 checks, through the power management unit 140, whether the voltage of the battery 110 is increasing. When the voltage of the battery 110 does not increase, since charging stops due to the input energy which is lower than the battery charging energy, the battery charging through power management is stopped, and a wake-up nerve stimulation message is sent to the nerve stimulation IC via the EN (S110).

Meanwhile, if only a magnetic field is absorbed by the magnetic field absorption unit 90, through the processes S40, S50, S60, and S70, when the magnetic field absorption unit is placed in areas where a magnetic field occurs, such as near an MRI device or an electric vehicle, the magnetic field absorption unit absorbs the magnetic field generated in that area, thereby minimizing the impact of the magnetic field on the user and preventing malfunction of the power management unit 140 and the stimulation electrode 70.

In addition, when only the input data related to the magnetic field value transferred from the magnetic field absorption unit 90 to the power management unit 140 is measured during the processes S20, S30, and S40, the magnetic field absorption unit 90 continuously absorbs only the magnetic field. So, the intensity of the magnetic field is very strong or the size of the magnetic field is very large, situations where the magnetic field penetrates the inserted body part 10 and induces malfunction in the stimulation electrode 70 and power management unit 140 may occur. Accordingly, the power management unit 140 and the stimulation electrode 70 can be stopped.

Therefore, the magnetic field absorption part 90 of the implantable nerve stimulation device according to an embodiment of the present disclosure can be utilized as as a malfunction prevention sensor to prevent malfunction of the power management unit 140 and the stimulation electrode 70.

The implantable nerve stimulation device according to an embodiment of the present disclosure can enhance implantation depth and allow for miniaturization.

Moreover, the implantable nerve stimulation device according to an embodiment of the present disclosure supplies power to a stimulation electrode using power generation elements which generate power based on friction from ultrasonic waves, thereby improving the power conversion efficiency of the ultrasonic waves, minimizing heat generation, and reducing the magnetic field generation of the power generation elements.

Furthermore, the implantable nerve stimulation device according to an embodiment of the present disclosure does not need for a separate device for electromagnetic radiation by reducing electromagnetic radiation due to the friction and vibration of the power generation elements.

While the exemplary embodiments of the present disclosure have been described in more detail with reference to the accompanying drawings, it will be understood by those of ordinary skill in the art that various modifications and equivalents may be made without deviating from the spirit or scope of the invention. Therefore, the above-described embodiments should be considered only as examples in all aspects and not for purposes of limitation.

This work was supported by the Next Generation Intelligence Semiconductor Foundation Program (20025736, Development of MICS SoC and platform for invivo implantable electroceutical device) funded By the Ministry of Trade, Industry & Energy (MOTIE, Korea).

This work (Grants No. S3282292) was supported by Business for Startup growth and technological development (TIPS Program) funded Korea Ministry of SMEs and Startups in 2022.

What is claimed is:

1. An implantable nerve stimulation device comprising:
    a body part which is formed of a metal that transmits ultrasonic waves, and includes a stimulation surface and a charging surface facing each other;
    a header part which is made of a non-metal and is located at one end of the body part;
    a cover which includes a stimulation electrode, a hinge part rotatably coupled to one side of the stimulation surface, and a coupling part detachably coupled to the side of the stimulation surface opposite the hinge part, is positioned above the stimulation surface to interpose a nerve between the electrode and the stimulation surface;
    power generation elements which are located inside the body part and are electrically connected to the electrode;
    a first connection part which extends from the coupling part;
    a second connection part which is provided at a connection point between the stimulation surface and the charging surface; and
    a connection member which binds the first connection part and the second connection part,
    wherein the first connection part includes a plurality of through-holes,
    wherein a portion of the second connection part is spaced apart from the connection point, and has an insertion space between the portion of the second connection part and the connection point,
    wherein the connection member includes a medical wire which continuously passes through at least one of the plurality of through-holes and the insertion space to bind and tighten the first connection part and the second connection part, wherein the power generation elements generate power based on friction caused by ultrasonic waves penetrating the charging surface, and includes an inducer vibrating by the ultrasonic waves, an electrified body generating frictional electricity by friction with the inducer, and a spacer interposed between the inducer and the electrified body to mutually separate the inducer and the electrified body.

2. The implantable nerve stimulation device according to claim 1, wherein the stimulation surface is covered with a non-metallic coating layer.

3. The implantable nerve stimulation device according to claim 2, wherein the non-metallic coating layer includes silicon.

4. The implantable nerve stimulation device according to claim 1, wherein the stimulation surface has a shape curved toward the inside of the body part, and wherein the charging surface has a flat shape.

5. The implantable nerve stimulation device according to claim 4, wherein the cover has a shape curved in a direction of moving away from the stimulation surface.

6. The implantable nerve stimulation device according to claim 1, wherein the stimulation electrode has a pattern shape with two or more curved portions.

* * * * *